United States Patent [19]
Weaver et al.

[11] Patent Number: 5,350,317
[45] Date of Patent: Sep. 27, 1994

[54] BATTERY PACK

[75] Inventors: Robert J. Weaver, Kirkland; Dennis C. Brittingham, Seattle; Joseph C. Basta, Bellevue; John C. Daynes, Redmond, all of Wash.

[73] Assignee: Physio-Control Corporation, Redmond, Wash.

[21] Appl. No.: 88,202

[22] Filed: Jul. 6, 1993

Related U.S. Application Data

[63] Continuation of Ser. No. 640,072, Jan. 11, 1991, Pat. No. 5,224,870.

[51] Int. Cl.$^5$ ............................................. H01R 3/00
[52] U.S. Cl. ..................................... 439/500; 439/350
[58] Field of Search ............... 439/152, 153, 157, 160, 439/500; 429/96-100

[56] References Cited

U.S. PATENT DOCUMENTS

| | | | |
|---|---|---|---|
| 2,731,586 | 1/1956 | Born | 439/500 |
| 3,865,101 | 2/1975 | Saper et al. | 128/2.06 R |
| 4,515,872 | 5/1985 | Okano | 429/65 |
| 4,590,943 | 5/1986 | Paull et al. | 128/419 D |
| 4,835,410 | 5/1989 | Bhagwat et al. | 439/500 |
| 4,871,629 | 10/1989 | Bunyea | 429/97 |
| 5,078,615 | 1/1992 | Benson et al. | 439/246 |

FOREIGN PATENT DOCUMENTS

| | | | |
|---|---|---|---|
| 0398607A1 | 11/1990 | European Pat. Off. | |
| 63-119156 | 5/1988 | Japan | |
| 2225178 | 5/1990 | United Kingdom | 439/500 |

Primary Examiner—David L. Pirlot
Attorney, Agent, or Firm—Christensen, O'Connor, Johnson & Kindness

[57] ABSTRACT

A battery pack (10) is disclosed for use with a medical instrument (12). The battery pack includes a housing (14), defined by a case (16) and cover (18). The housing includes a storage section (22), for receiving batteries (78 and 80), and a connector section (24) on one side of the storage section for cooperating with a latch assembly (110), ejection spring (142), and electrical connectors (108) provided adjacent a battery tray (98) on the instrument. Specifically, the connector section includes an aligned latch surface (64), ejection surface (62), and electrical connectors (86) that cooperatively engage the latch assembly, ejection spring, and connectors on the instrument. As a result, the battery pack can be quickly, easily, and effectively attached to the instrument, in spite of the side-mounted nature of the connector section. Further, the relative weight and alignment of the battery pack and instrument are such that the center of mass of the instrument, with a battery pack inserted into the tray, is aligned with the instrument's handle (96).

4 Claims, 8 Drawing Sheets

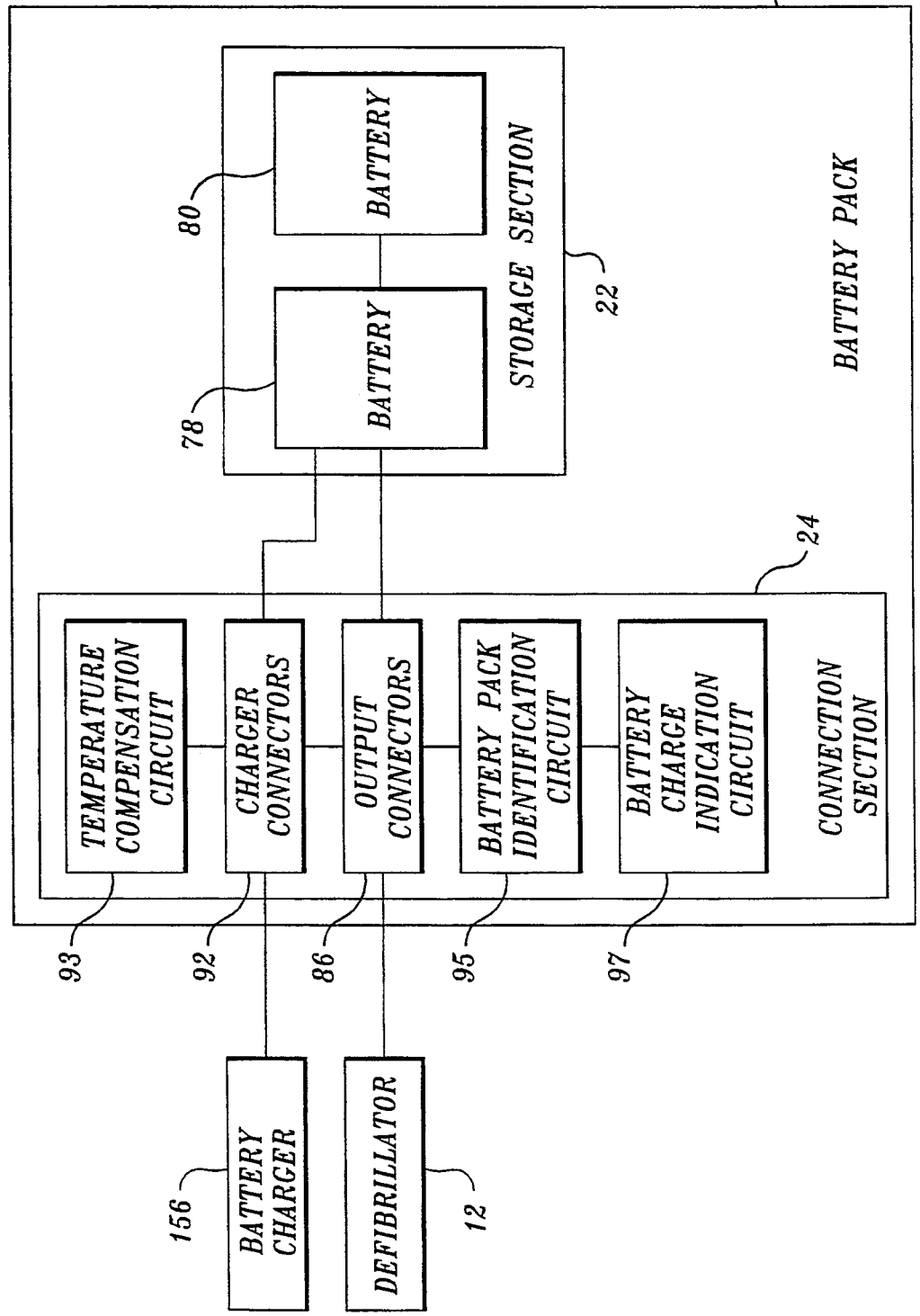

BATTERY PACK

This is a continuation of the prior application Ser. No. 07/640,072, filed on Jan. 11, 1991, now U.S. Pat. No. 5,224,870 of Robert J. Weaver, Dennis C. Brittingham, Joseph C. Basta, and John C. Daynes for BATTERY PACK, the benefit of the filing date of which are hereby claimed under 35 U.S.C. §120.

FIELD OF THE INVENTION

This invention relates generally to battery packs and, more particularly, to connections for coupling battery packs to instruments.

BACKGROUND OF THE INVENTION

Batteries are widely used to provide electrical energy to portable devices. Although batteries are available in a variety of conventional sizes, shapes, and ratings, many devices are intended for use with only specially designed battery packs. While battery packs are often more expensive than conventional batteries, the use of battery packs may be preferable for a number of reasons.

For example, a battery pack may include storage cells designed to satisfy the particular power requirements of a device with which the battery pack will be used. Battery packs can also be designed to be coupled to the device more quickly, easily, and effectively than conventional batteries. Further, along with the storage cells, a battery pack may house additional components useful to the device and unavailable with standard batteries. Finally, the battery pack housing may provide better mechanical and environmental protection for the storage cells than is available with conventional batteries.

One application for battery packs that is of particular interest is the powering of medical instruments. As will be appreciated, a medical instrument may be used in emergency situations in which the instrument's power source must be absolutely dependable. However, as a battery pack is used, the energy stored by the battery pack is necessarily depleted and will eventually become inadequate to power the medical instrument. Unless the instrument is no longer needed or can be connected to an auxiliary source of power, the discharged battery pack must be removed and a charged battery pack inserted in its place. To minimize the resultant disruption in the instrument's operation, the battery pack employed must be quickly and easily replaceable.

One example of a medical instrument employing battery packs of the type described above is the LIFEPAK 5 portable defibrillator and ECG monitor sold by Physio-Control Corporation, the assignee of the present application. The defibrillator and ECG monitor can be interlocked or used independently and each is designed to be powered by a rechargeable battery pack.

In that regard, the battery packs are received within stowage recesses provided adjacent one corner of the defibrillator and one corner of the monitor. Each recess includes a floor, an end wall, and two sidewalls and is partially open at a connector end. A pair of male electrical connector posts are provided in the floor of the recess. The posts are located adjacent the connector end of the recess, spaced apart from the sidewalls.

The battery packs used with the defibrillator and monitor are interchangeable and have a substantially uniform rectangular cross section. Each battery pack has a top, a bottom, a beveled end, a connector end, and a pair of sidewalls. A pair of electrical receptacles are provided in the bottom of each battery pack, adjacent the connector end of the battery pack. The receptacles are designed to attach to the connector posts located in the recess.

Also provided at the connector end of the battery pack is a latch arm. The latch arm is molded as an integral part of the battery pack and extends upwardly from the bottom of the battery pack, midway between the two connectors. The free end of the latch arm is resiliently depressible toward the battery pack and includes a detent for engaging the recess, as will be described below.

A battery pack is connected to the defibrillator or monitor by first inserting the beveled end of the battery pack into the appropriate battery stowage recess. Then, the connector end of the battery pack is inserted into the connector end of the recess, causing the posts on the floor of the recess to electrically and mechanically engage the receptacles in the bottom of the battery pack. As this occurs, the free end of the latch arm on the battery pack is deflected by a lip included at the connector end of the receptacle. Given its resilient nature, the latch arm deflects until further insertion of the battery pack allows the detent on the free end of the latch arm to clear the lip, securely retaining the battery pack in the recess.

To remove the battery pack, the free end of the latch arm must be manually depressed to again allow the detent to clear the lip. Another lip located at the connector end of the battery pack then allows the battery pack to be lifted from the recess.

As will be appreciated, the particular battery pack described above is only one of a multitude of battery packs designed for various applications. Often, however, existing battery packs are not suitable for use with newly developed instruments and it is desirable to develop a new battery pack that can be quickly and easily attached to the instrument, that satisfies the power requirements of the instrument, and that does not disturb the general ergonomics of the instrument.

SUMMARY OF THE INVENTION

In accordance with one aspect of this invention, a battery pack, having a center of mass, is disclosed for use with a medical instrument that includes a latch, an ejector, and an electrical connector. The battery pack includes an energy storage device for storing electrical energy. A latch engagement surface, ejector engagement surface, and connector engagement device are coupled to the energy storage device. The latch engagement surface is included for engaging the latch. The ejector engagement surface is included for engaging the ejector. The connector engagement device is included for engaging the connector. The latch engagement surface, ejector engagement surface, and connector engagement device are substantially aligned in a plane offset from the center of mass of the battery pack.

In accordance with an alternative aspect of this invention, a medical instrument is provided for use with a battery pack. The instrument includes a housing and a handle, coupled to the housing, for allowing the medical instrument to be carried by a user. A battery stowage tray is provided in the housing of the instrument for receiving the battery pack. The battery stowage tray is positioned so that the center of gravity of the medical instrument is substantially aligned with the handle of the instrument when a battery pack is received by the battery stowage tray.

A latch, coupled to the housing adjacent the battery stowage tray, is included for releasably engaging a battery pack when the battery pack is received by the battery stowage tray. Similarly, an ejection device, coupled to the housing adjacent the battery stowage tray and aligned with the latch, is included for applying a force to a battery pack when the battery pack is received by the battery stowage tray. An electrical connector is coupled to the housing adjacent the battery stowage tray and is aligned with the ejection device, for electrically connecting the battery pack to the instrument. In a preferred arrangement, the latch is a biased latch; the ejection device is a spring; and a plurality of electrical connectors are employed. The latch, spring, and plurality of electrical connectors are positioned about a common centerline.

In accordance with a more detailed aspect of the invention, the battery pack includes a storage compartment and a connector compartment. The storage compartment is shaped roughly like a parallelepiped and has a top surface, bottom surface, front surface, back surface, first side, and second side. A storage device, for storing energy for discharge to the instrument, is received within the storage compartment. The connector compartment is provided on the first side of the storage compartment and has a connector surface, a latch surface, and an ejection surface, each of which are substantially parallel to the front of the storage compartment. The connector surface of the connector compartment is spaced from the plane of the front of the storage compartment by a first distance. The latch surface of the connector compartment is spaced from the plane of the front of the storage compartment by a second distance that is greater than the first distance. The ejection surface of the connector compartment is spaced from the plane of the front of the storage compartment by a third distance that is greater than the second distance. The latch surface of the connector compartment is for cooperatively engaging the latch of the instrument and the ejection surface of the connector compartment is for cooperatively engaging the ejection mechanism of the instrument. Finally, an electrical connector, physically coupled to the connector surface of the connector compartment and electrically connected to the storage device, is included for providing an electrical connection to the instrument.

BRIEF DESCRIPTION OF THE DRAWINGS

The invention will presently be described in greater detail, by way of example, with reference to the accompanying drawings, wherein:

FIG. 8 is a block diagram illustrating the battery pack, medical instrument, and a recharger.

DETAILED DESCRIPTION OF THE PREFERRED EMBODIMENT

Figure 1:
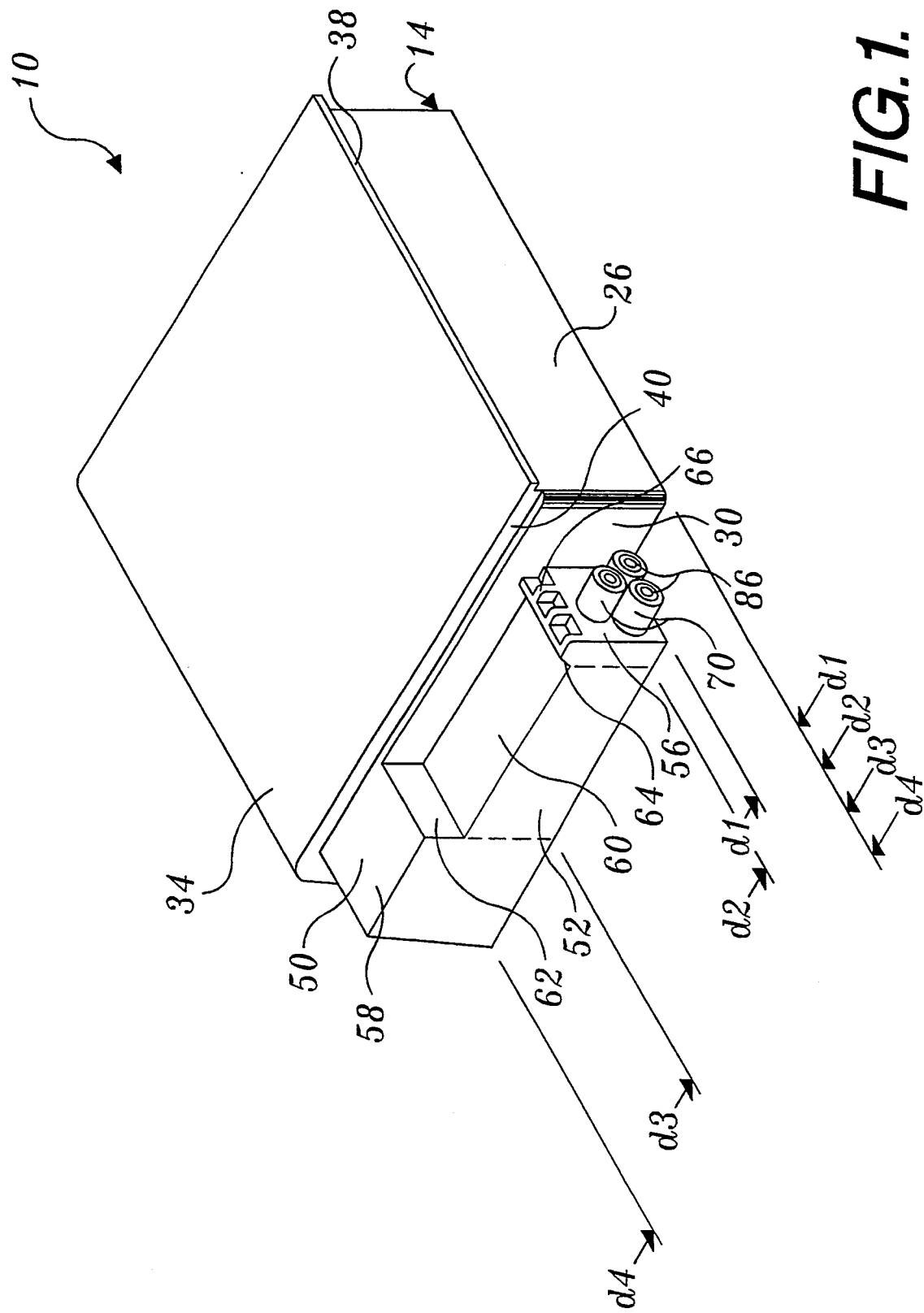
FIG. 1 illustrates a battery pack constructed in accordance with this invention and including a battery storage section and a connector section.

A battery pack 10, designed for use with a medical instrument 12, is shown in FIG. 1. The battery pack 10 is a portable power source that provides the energy required by instrument 12 for proper operation. With the inclusion of battery pack 10, the instrument 12 can be used, for example, in field locations that do not have alternative sources of power available.

As will be described in greater detail below, the battery pack 10 is designed to offer a number of advantageous features. For example, because the housing of the battery pack 10 performs guidance, latching, and ejection functions, these features are achieved by a battery pack 10 that is mechanically simple. The latching, connection, and ejection features of the battery pack 10 are also aligned, albeit along an axis that is offset from the center of mass of the battery pack 10, to ensure that the battery pack 10 can be smoothly inserted into, and removed from, instrument 12. When constructed in this manner, the battery pack 10 can be quickly and easily removed from instrument 12 and a replacement battery pack securely substituted in its place.

Reviewing the construction of the battery pack 10 in greater detail, the primary structural component of the battery pack 10 is a housing 14, shown in FIG. 1. The housing 14 is formed by a case 16 and a cover 18, shown in FIG. 2, which are secured together by ultrasonic welding and a pair of fasteners 20. As will be discussed in greater detail below, the case 16 and cover 18 cooperatively protect the other components of battery pack 10 both mechanically and electrically. In addition, the case 16 plays a key role in the alignment, latching, and ejection of battery pack 10 relative to instrument 12.

Addressing these components of the battery pack housing 14 individually, the case 16 is divided into a storage section 22 and a connector section 24. The storage section 22 houses those components of battery pack 10 that store the energy required by instrument 12 for proper operation. The connector section 24 of the case 16, on the other hand, houses those components required to recharge the battery pack 10 and interface it with instrument 12.

The storage section 22 of case 16 is defined by a rectangular front surface 26, rectangular back surface 28, first side 30, rectangular second side 32, square top surface 34, and an open bottom 36. The top surface 34 of the storage section 22 includes a narrow lip 38 that projects from, and extends the length of, the front surface 26 of section 22. A first side recess 40 is provided in the corner defined by the top surface 34 and first side 30 of the storage section 22. Similarly, a second side recess 42 is provided in the corner defined by the top surface 34 and second side 32 of storage section 22. Both recesses 40 and 42 extend the length of case 16.

The top surface 34 of the storage section 22 of case 16 is also provided with a pair of cover fastener mounting posts 44, positioned inside case 16 and projecting toward the open bottom 36. The posts 44 are located in a plane spaced roughly half way between the first side 30 and second side 32 of the storage section 22, dividing section 22 into first and second cell-receiving chambers 46 and 48. As described in greater detail below, the projecting ends of posts 44 are designed to engage the cover fasteners 20 and may, for example, include threaded openings.

Reviewing now the construction of the connector section 24 of the battery pack case 16, as shown in FIG. 1, the connector section 24 extends from the first side 30 of the storage section 22 of case 16. The connector section 24 includes a top wall 50, sidewall 52, back wall 54, front wall 56, and is open at its bottom and at the first side 30 of the storage section 22.

The top wall 50 of the connector section 24 is divided into a number of joined surfaces, including an upper surface 58, lower surface 60, ejection surface 62, latch surface 64, and lift surface 66. The upper surface 58 of the top wall 50 couples sidewall 52 to the first side 30 of the storage section 22. The upper surface 58 is generally parallel to, and spaced apart from, the top surface 34 of storage section 22 by a distance equal to the depth of the recess 40 in the storage section 22.

The lower surface 60 of the top wall 50 also couples the sidewall 52 of the connector section 24 to the first side 30 of the storage section 22. The lower surface 60 is generally parallel to the upper surface 58 and is spaced apart therefrom by a distance equal to the height of the ejection surface 62. In that regard, the ejection surface 62 joins the front end of the upper surface 58 and and the back end of the lower surface 60 of the top wall 50. As shown in FIG. 1, the ejection surface 62 is substantially perpendicular to surfaces 58 and 60.

The latch surface 64 of the top wall 50 extends from the front end of the lower surface 60 at an angle, defined with respect to the lower surface 60, that is slightly greater than 90 degrees. The height of the latch surface 64 is roughly only one-fourth that of the ejection surface 62. The final portion of the top wall 50 is the rounded lift surface 66, which curves downward and forward from the top of latch surface 64 to the front wall 56 of the connector section 24.

The sidewall 52 of the connector section 24 of case 16 is roughly L-shaped, as shown in FIG. 1. Sidewall 52 is parallel to the first side 30 of the storage section 22 and is joined thereto by the top wall 50, back wall 54, and front wall 56.

The back wall 54 extends substantially perpendicularly between sidewall 52 of the connector section 24 and the first side 30 of the storage section 22. The back wall 54 is also joined to the upper surface 58 of the top wall 50, at an angle of slightly greater than 90 degrees. Positioned roughly in the center of the back wall 54 is a recharger connector opening 68.

The last wall of the connector section 24 to be discussed is the front wall 56. The front wall 56 extends generally perpendicularly between the first side 30 of the storage section 22 and the sidewall 52 of the connector section 24. The front wall 56 includes three cylindrical connector supports 70, projecting perpendicularly therefrom. The connector supports 70 are arranged in a pattern in which the axes of the three supports define the corners of an equilateral triangle, one side of which is adjacent and parallel to the bottom of the front wall 56. As will be further appreciated, a vertical reference plane that bisects the ejection surface 62 and latch surface 64 will also bisect the top one of the supports 70 and be spaced midway between the lower two supports 70.

Addressing the relative position of several of these features, the connector supports 70 are positioned a first distance d1 reaward of the front surface 26 of the case storage section 22. Similarly, the latch surface 64 is generally located a second distance d2 rearward of front surface 26. In addition, the ejection surface 62 is positioned a third distance d3 rearward of the front surface 26. In the preferred arrangement, d3 is greater than d2, which is greater than d1. As will be described in greater detail below, this relative orientation of features responsible for connection, latching, and ejection has been found particularly effective and efficient.

The other component of the housing 14 to be discussed is cover 18. The cover 18 is constructed to cover the bottom of both the storage and connector sections 22 and 24 of the case 16. The cover 18 includes a pair of roughly parallel, spaced-apart, instrument clearance recesses 72, located on the portion of cover 18 that closes the storage section 22 of the case 16. As will be appreciated, the recesses 72 will be located on the bottom of the assembled battery pack 10 and their width increases as the front of the battery pack 10 is approached, while their depth decreases.

The cover 18 also includes a pair of spaced-apart fastener openings 76, located between the two clearance recesses 72. The openings 76 are positioned so that, with the cover 18 placed against the case 16, the openings 76 will align with the cover fastener mounting parts 44 provided on the case 16. As a result, the cover 18 can be secured to the case 16 by fasteners 20, after ultrasonic welding.

Figure 2:
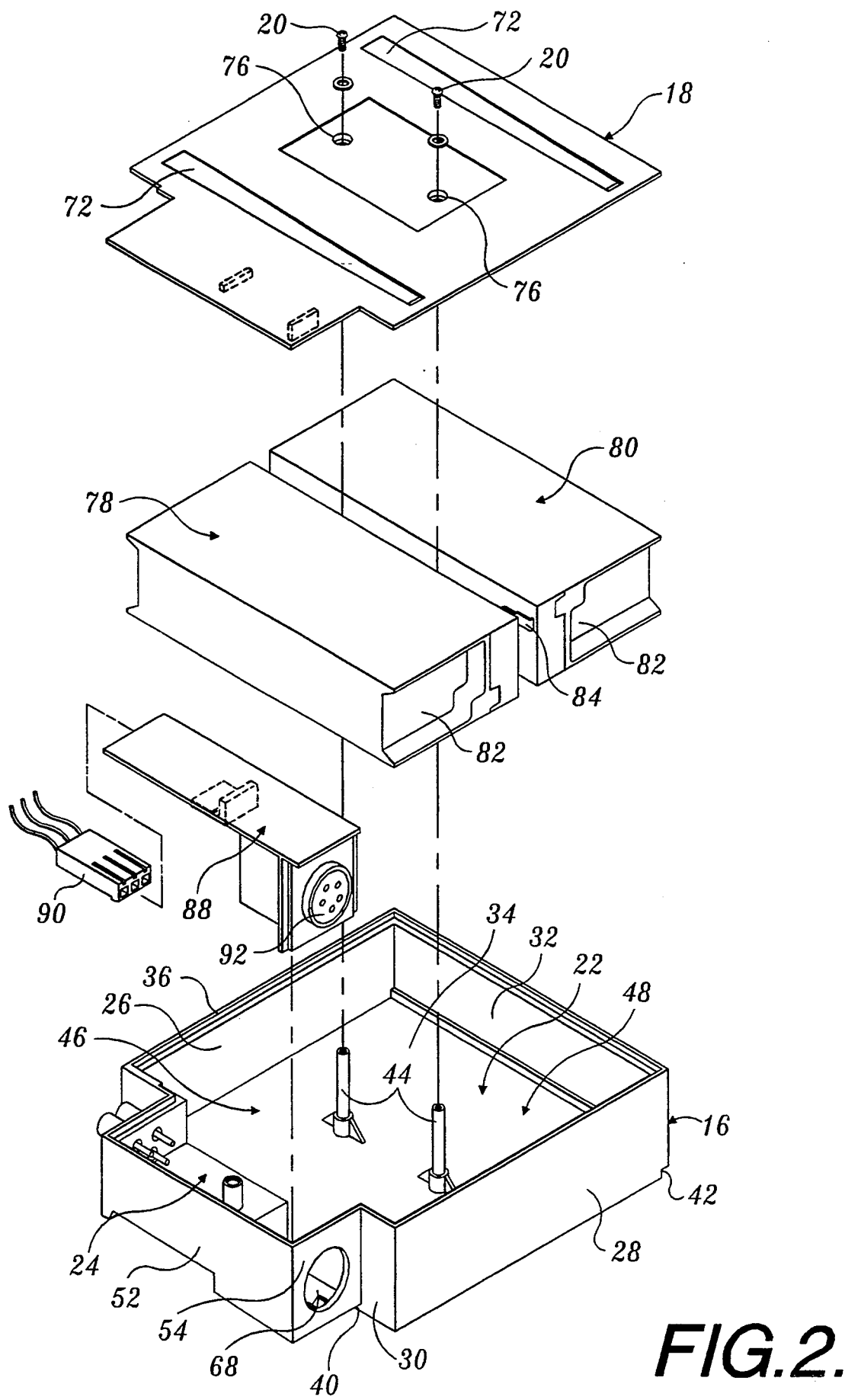
FIG. 2 is an exploded view of the battery pack of FIG. 1.

Having reviewed the construction of the housing 14, the components of battery pack 10 included within housing 14 will now be discussed in greater detail. In that regard, as shown in FIG. 2, a pair of batteries 78 and 80 are received within the storage section 22 of the case 16, on opposite sides of the fastener mounting posts 44. Each battery 78 and 80 includes a storage cell 82 and two terminals 84. As will be appreciated, the storage cells 82 employed may be, for example, sealed lead acid (SLA) or nickel-cadmium (NiCad) cells. The two batteries 78 and 80 are coupled in series to provide a 3.4 ampere-hour, 12-volt power source.

Figure 3:
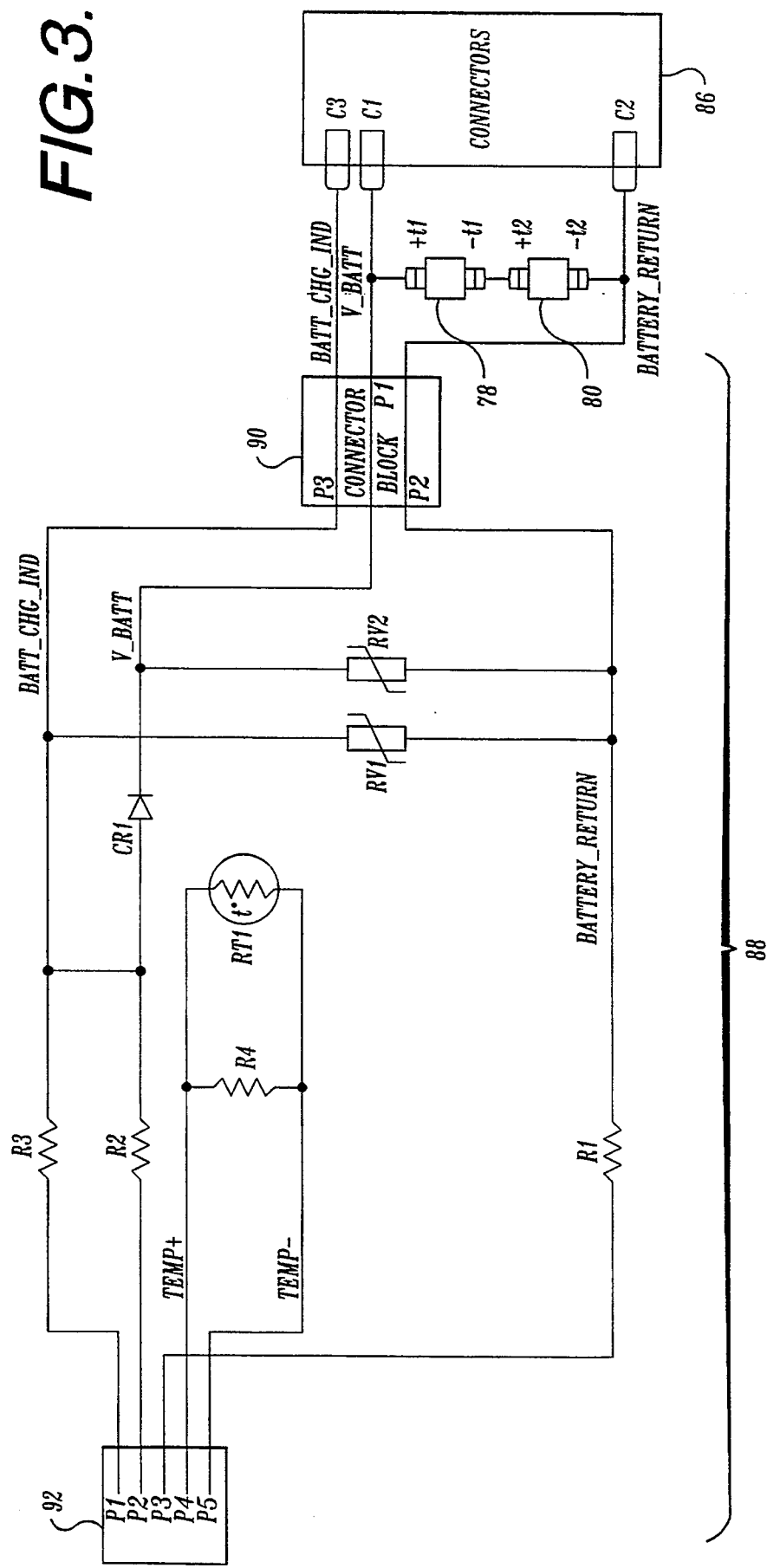
FIG. 3 is a schematic diagram of the battery pack of FIG. 1.

An electrical connection between the series-coupled batteries 78 and instrument 12 is achievable with the aid of three female electrical connectors or receptacles 86. More particularly, as shown in the schematic diagram of FIG. 3, the positive terminal +t1 of battery 78 is connected to a first one c1 of connectors 86; the negative terminal −t1 of battery 78 is connected to the positive terminal +t2 of battery 80; and the negative terminal −t2 of battery 80 is connected to a second one c2 of the connectors 86. The third one c3 of connectors 86 is not directly connected to batteries 78 and 80. The connectors 86 are received within, and supported by, the connector supports 70 provided on the connector section 24 of case 16.

The next component of the battery pack 10 to be discussed is a printed circuit board assembly 88, housed in the connector section 24 of case 16. The board assembly 88 includes a number of components employed in the charging of the battery pack 10. For example, assembly 88 includes a three-pin connector block 90 that provides an electrical interface with connectors 86 and, hence, to the batteries 78 and 80. In that regard, a first pin p1 of block 90 is connected to the c1 connector 86; a second pin p2 of block 90 is connected to the c2 connector 86; and a third pin p3 of block 90 is connected to the c3 connector 86.

Block 90 is also connected to several other components of the board assembly 88. More particularly, the anode terminal of a blocking; diode CR1 is connected to pin p3 of connector block 90, while its cathode terminal is connected to pin p1. As will be appreciated from the discussion below, the diode CR1 prevents the series-coupled batteries 78 and 80 from discharging through a battery charger in the event that an unpowered charger is connected to battery pack 10. Diode CR1 also prevents the series-coupled batteries 78 and 80 from lighting a charge indicator light included on the instrument 12, while allowing the indicator light to be lit when a recharger is connected to the battery pack 10.

A 22-volt, metal-oxide varistor (MOV), designated RV1, is coupled between pins p3 and p2 of block 90. Similarly, a second MOV RV2 is connected between pins p1 and p2 of block 90. The MOVs RV1 and RV2 are included to prevent ESD from radiating out through the charger cord.

The assembly 88 also includes a five-pin connector block 92, which allows the battery pack 10 to be attached to a recharger 156, shown in block form in FIG. 8. Reviewing the various connections to block 92, a resistor R1 is connected between pin p3 of the connector block 92 and pin p2 of connector block 90. In the event that (SLA) storage cells 82 are employed, another resistor R2 is connected between pin p2 of connector block 92 and the anode terminal of diode CR1. Alternatively, if NiCad storage cells 82 are employed, a resistor R3 is connected between pin p1 of the five-pin connector block 92 and the anode terminal of diode CR1. In the event that RFI exiting the battery pack via the connections to recharger 156 becomes problematic, these resistances would be removed from the assembly and radio-frequency (RF) chokes installed in their places.

Two of the more important components of assembly 88 are a resistor R4 and a thermistor RT1. The resistor R4 and thermistor RT1, which collectively form part of a temperature compensation circuit 93 shown in FIG. 8, are connected in parallel between pins p4 and p5 of connector block 92 and are selected in accordance with the particular charger to be employed and allow the charger to compensate for the effect of ambient temperature on the charging process. In that regard, battery pack 10 is intended for use with a charger that is operable in a fail-safe mode in which the output voltage of the charger will drop to a low level if an open thermistor circuit is sensed. As a result, continuous overcharge of the battery pack 10 is prevented.

As will be appreciated, in addition to the temperature compensation circuit 93, as shown in FIG. 8, the circuit board assembly 88 may also include additional components. For example, board assembly 88 may include a battery pack identification circuit 95 that employs a coding scheme to allow the instrument 12 or recharger to identify the battery pack 10 and store the information in a file that records battery usage or maintenance.

In addition, the board assembly 88 may include a battery-charging indication circuit 97, if desired. Such a circuit 97 would allow the status of the battery pack's charge to be monitored and an output produced for use by an operator in establishing the readiness of battery pack 10 for use.

Having reviewed the construction of the battery pack 10, the medical instrument 12 will now be considered in greater detail. As will be appreciated, the medical instrument 12 may be any one of a variety of devices that requires electrical energy from a portable and replaceable source. In the preferred arrangement, however, the medical instrument 12 is a defibrillator/monitor used to monitor the electrical activity of a patient's heart and, if necessary, apply a pulse of energy to the heart to restore it to proper operation.

Figure 4:
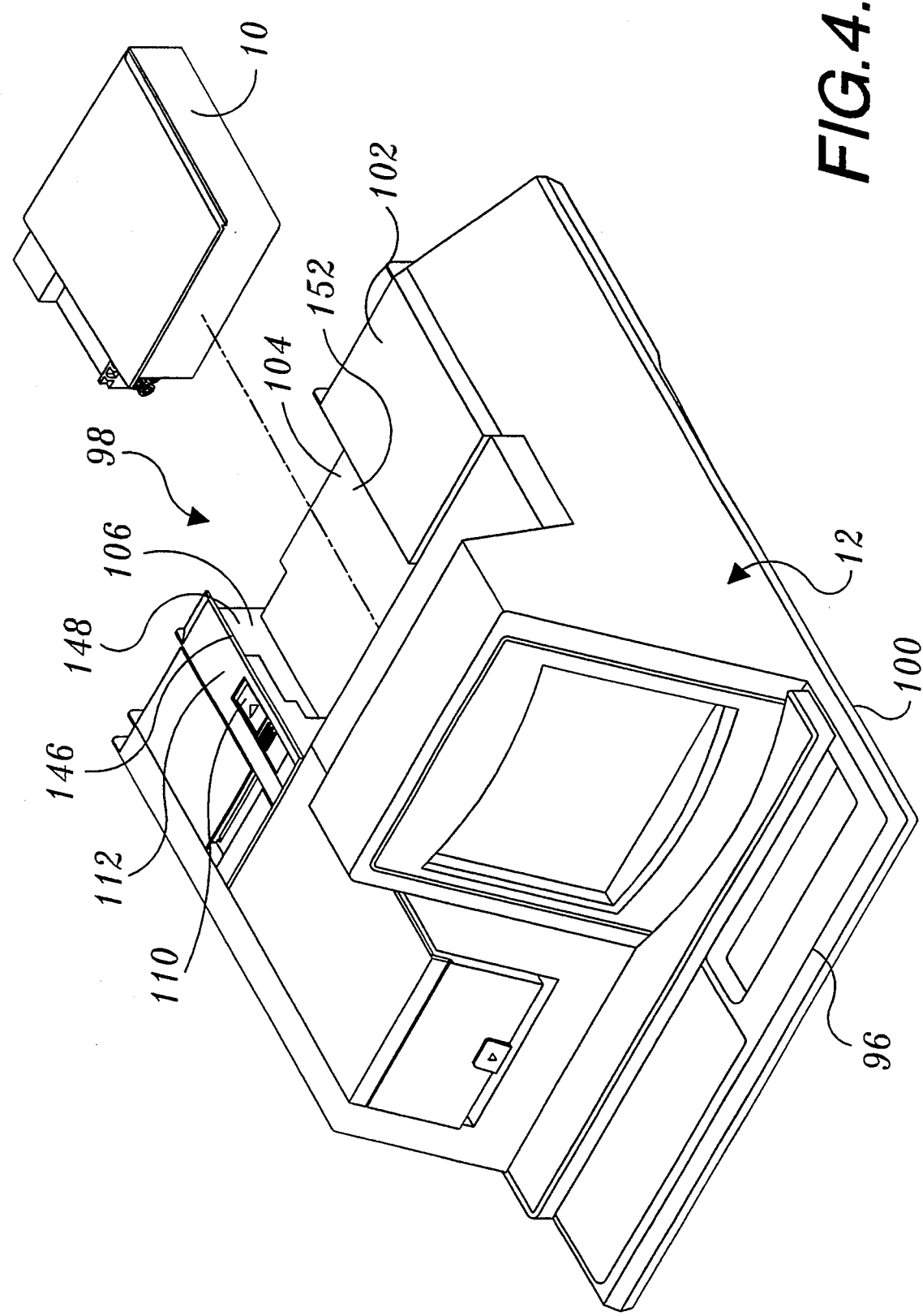
FIG. 4 illustrates the battery pack of FIG. 1 inserted into a medical instrument.

Referring now to FIG. 4, a defibrillator/monitor 12 is shown for use with battery pack 10. As will be appreciated, the defibrillator/monitor 12 includes a body 94, which houses the various components required to administer defibrillation pulses to a patient, and a handle 96 that allows the defibrillator/monitor 12 to be easily carried by an operator. The battery pack 10 is received within a tray 98 provided in the body 94 of defibrillator/monitor 12.

Reviewing the layout of the defibrillator/monitor 12 in greater detail, the handle 96 is located at the forward end of the bottom surface 100 of the defibrillator/monitor 12, adjacent one corner. The tray 98, on the other hand, is located in the upper surface 102 of the defibrillator/monitor 12, roughly midway between its two sides. As will be described below, the location of tray 98, in cooperation with the mass of the battery pack 10 and the distribution of the various components in defibrillator/monitor 12, causes the center of mass of the defibrillator/monitor 12 to be positioned substantially in line with the handle 96 when the battery pack 10 is inserted into tray 98. As a result, the defibrillator/monitor 12 is relatively easy to carry.

Like the battery pack 10, tray 98 includes a storage section 104 and connector section 106. The storage section 104 of tray 98 is dimensioned to receive the storage section 22 of the battery pack case 16, while the connector section 106 of tray 98 is dimensioned to receive the connector section 24 of case 16. The connector section 106 has associated therewith the various components of the defibrillator/monitor 12 that retain, eject, and provide electrical connection to the battery pack 10.

Figure 5:
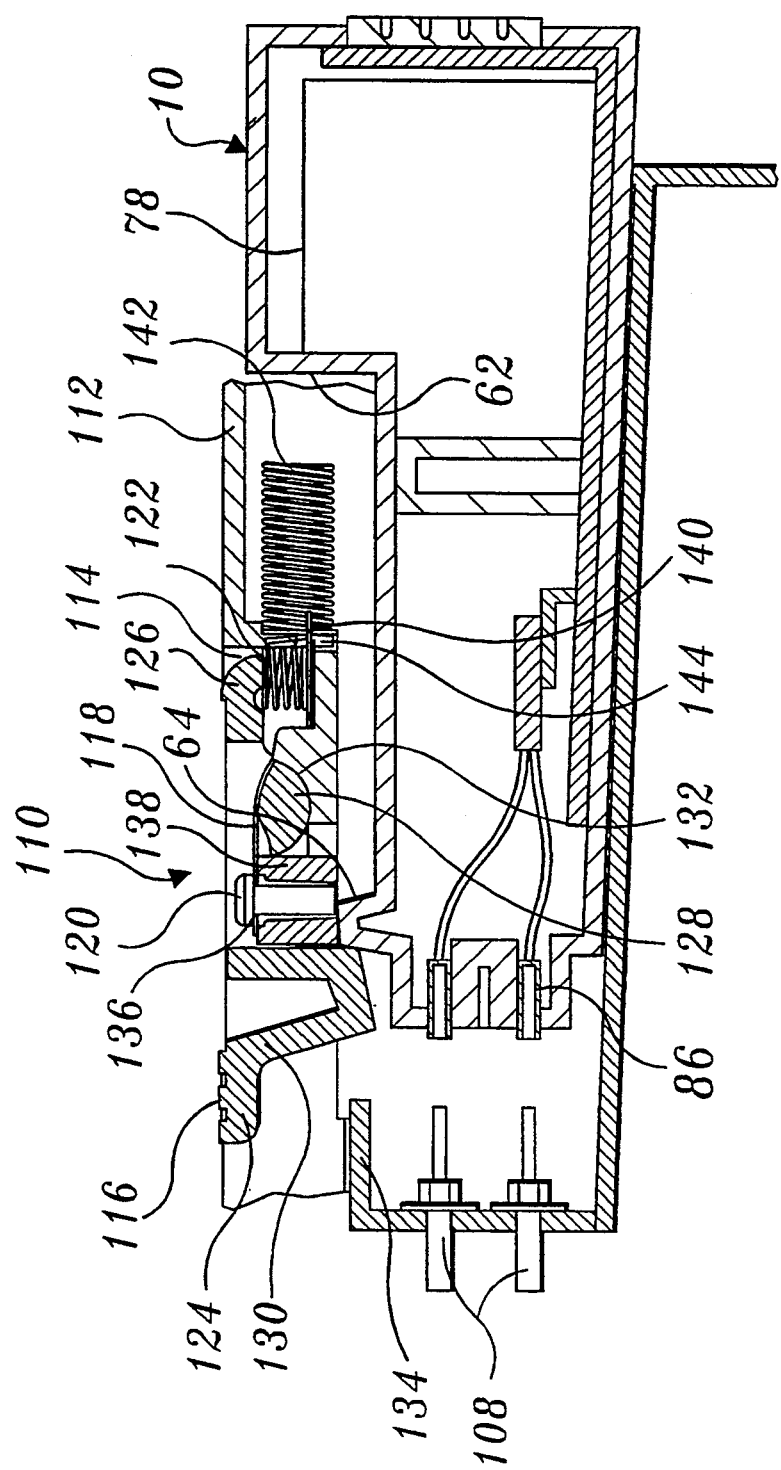
FIGS. 5, 6, and 7 are partial cross-sectional views showing the battery pack at various states of insertion into the medical instrument.

In that regard, three male electrodes 108 designed to cooperatively engage the female connectors 86 on battery pack 10 are located on an inner surface of the connector section 106 of tray 98, as shown in FIG. 5. The electrodes 108 are aligned in a triangular arrangement corresponding to that of the battery pack connectors 86. The connectors 86 and electrodes 108 mate in a relatively highfriction fit to ensure good electrical connection of the battery pack 10 to the defibrillator/monitor 12.

A latch assembly 110 is also provided on the defibrillator/monitor 12 adjacent the connector section 106 of tray 98. As shown, the defibrillator/monitor 12 includes a housing 112 that extends over the connector section 106 of tray 98 and supports the latch assembly 110. More particularly, the components of the latch assembly 110 are received within a latch recess 114 provided in the housing 112. These components include a latch arm 116, latch capture spring 118, latch retention screw 120, and latch bias spring 122.

Addressing these components individually, reference is made to FIGS. 4, 5, 6, and 7. As shown, the latch arm 116 includes a lift tab 124 provided at one end and a bias tab 126 provided at the other end. A latch pivot bar 128 is located between the lift tab 124 and bias tab 126. Similarly, a latch projection 130 is located between the pivot bar 128 and lift tab 124.

The lower surface of the pivot bar 128 is curved and pivotably resides in a curved pivot bar recess 132, included as part of the latch recess 114. As the latch arm 116 pivots, the latch projection 130 extends through, and is withdrawn from, a latch projection opening 134 that couples the latch recess 114 to the connector section 106 of tray 98. As will be described in greater detail, the latch projection 130 is thus able to cooperatively engage the latch surface 64 provided on the battery pack case 16.

The latch arm 116 is retained in the latch recess 114 by the capture spring 118 and retention screw 120. In that regard, the capture spring 118 is a leaf-type spring that includes a curved step, positioned roughly midway between the two ends of spring 118, which contacts the pivot bar 128. One end of the capture spring 118 is provided with an opening 136 through which the retention screw 120 passes before being secured to a retention screw mount 138, included as part of recess 114. The other end of capture spring 118 includes a pair of spaced-apart ejection spring slots 140 and extends under the bias tab 126 of latch arm 116 before projecting through an opening in recess 114. With the capture spring 118 retained against the pivot bar 128 by the cooperative action of the retention screw 120 and the opening in the recess 114, the latch arm 116 is securely retained in the latch recess 114.

The bias spring 122 is located between the bias tab 126 of latch arm 116 and the free end of the capture spring 118. One end of the cylindrical bias spring 122 receives the bias tab 126 of latch arm 116. The other end of bias spring 122 resides against the capture spring 118.

Reviewing the basic operation of these components of the latch assembly 110, the latch arm 116 is normally flush with the surface of the defibrillator/monitor housing 112, as shown in FIG. 5. In this position, the bias spring 122 is forcing the bias tab 126 of latch arm 116 upward and the latch projection 130 is pivoted downward through the projection opening 134. By lifting the latch arm lift tab 124, the latch arm 116 pivots in the opposite direction about bar 128, causing the bias tab 126 to compress the bias spring 122 and the latch projection 130 to withdraw from the projection opening 134.

A cylindrical ejection spring 142 is also included on the defibrillator/monitor 12 and projects from the inner surface of the connector section 106 of tray 98. A projecting end of the ejection spring 142 is free to move along an axial line extending substantially parallel to the sides of tray 98. An attached end of the ejection spring 142 is coupled to the defibrillator/monitor 12 by an ejection spring retention tab 144, included as part of the latch recess 114, that restrains the attached end from moving axially. Alignment of the ejection spring 142 is also maintained by the ejection spring engagement slots 140 provided in the end of capture spring 118. In that regard, the slots 140 engage a section of the ejection spring 142, adjacent the attached end, at two locations spaced 180 degrees apart.

Together, the retention tab 144 and engagement slots 140 support the ejection spring 142 axially and symmetrically about a reference plane that extends parallel to the sides of the tray 98 and that generally divides the connector section 106 of tray 98 in half. The same reference plane is axially aligned with the tray connector electrodes 108 and symmetrically divides the top electrode 108, while passing midway between the lower two electrodes 106.

Referring to FIGS. 4, 5, 6, and 7, the insertion of a battery pack 10 into the tray 98 of defibrillator/monitor 12 will now be described. The front surface 26 of the battery pack housing 12 is first introduced into the tray 98. Lips 146, provided in the defibrillator/monitor housing 112 on both sides of tray 98, cooperatively engage the recesses 40 and 42 in the top surface 34 of the battery pack 10. The lips 146 help maintain a desired alignment of the battery pack 10 and tray 98 during insertion, and also restrict movement of the battery pack 10 along a line normal to the top surface 34 of battery pack 10.

The sides 148 of the tray 98 also cooperate with the first and second sides 30 and 32 of the battery pack 10 to guide the battery pack 10 during insertion. As will be appreciated, the sides 148 of tray 98 further restrict movement of battery pack 10 along a line that is normal to the first and second sides 30 and 32. The clearance recesses 72 provided in the cover 18 allow the battery pack 10 to be inserted into tray 98 without interference.

As the battery pack 10 is inserted into tray 98, the battery pack 10 is secured in tray 98 by the latch assembly 110, restricting its movement along the line of insertion. More particularly, as shown in FIG. 5, the lift surface 66 provided adjacent the front end of the connector section 24 of battery pack 10 first contacts the latch projection 130 provided on the latch arm 116. The latch projection 130 is angled to allow the lift surface 66 to easily raise the latch projection 130. In that regard, the force of insertion is translated to the latch arm 116, compressing the bias spring 122 and allowing the latch projection 130 to rise.

Figure 6:
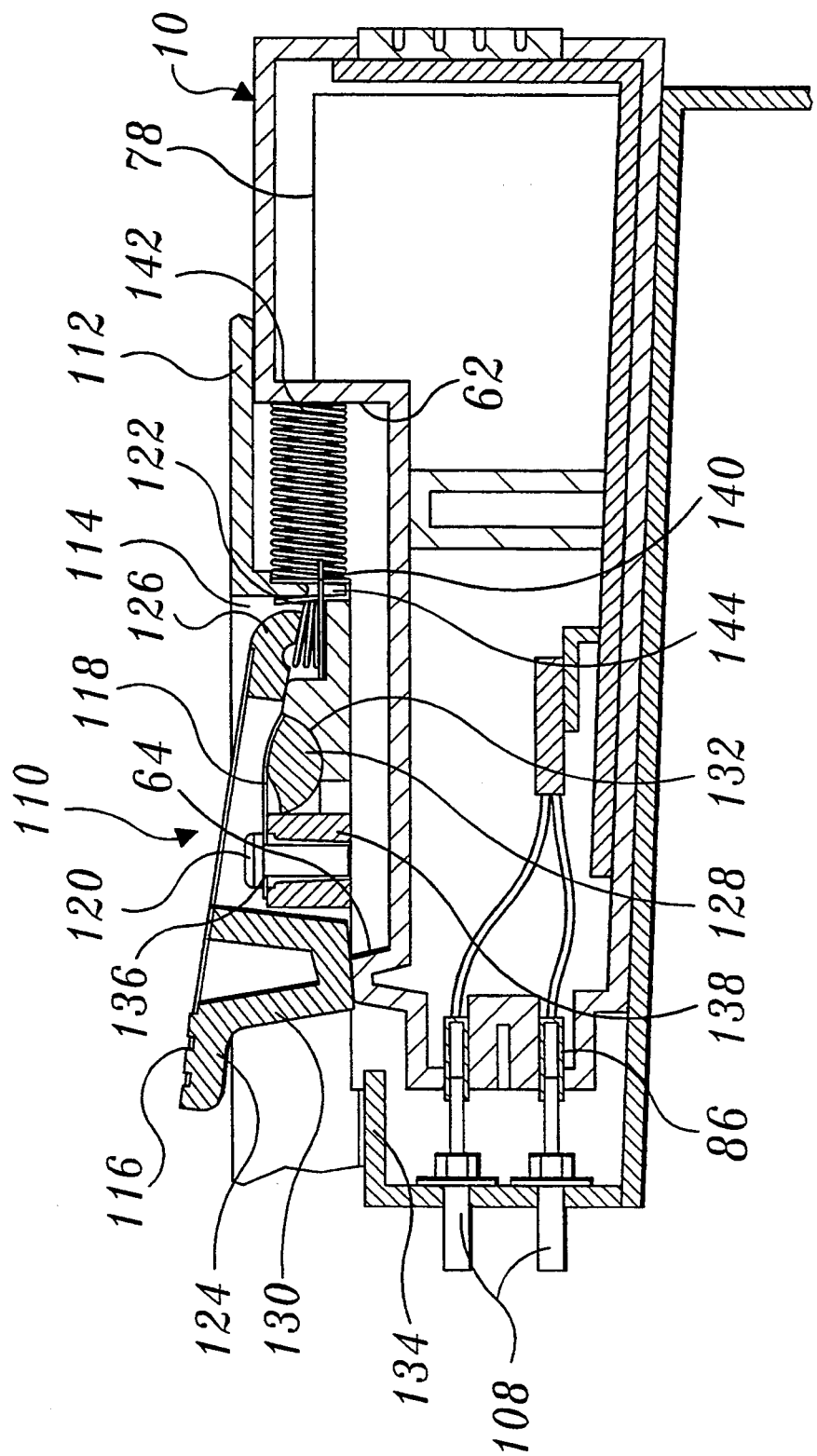
Figure 7:
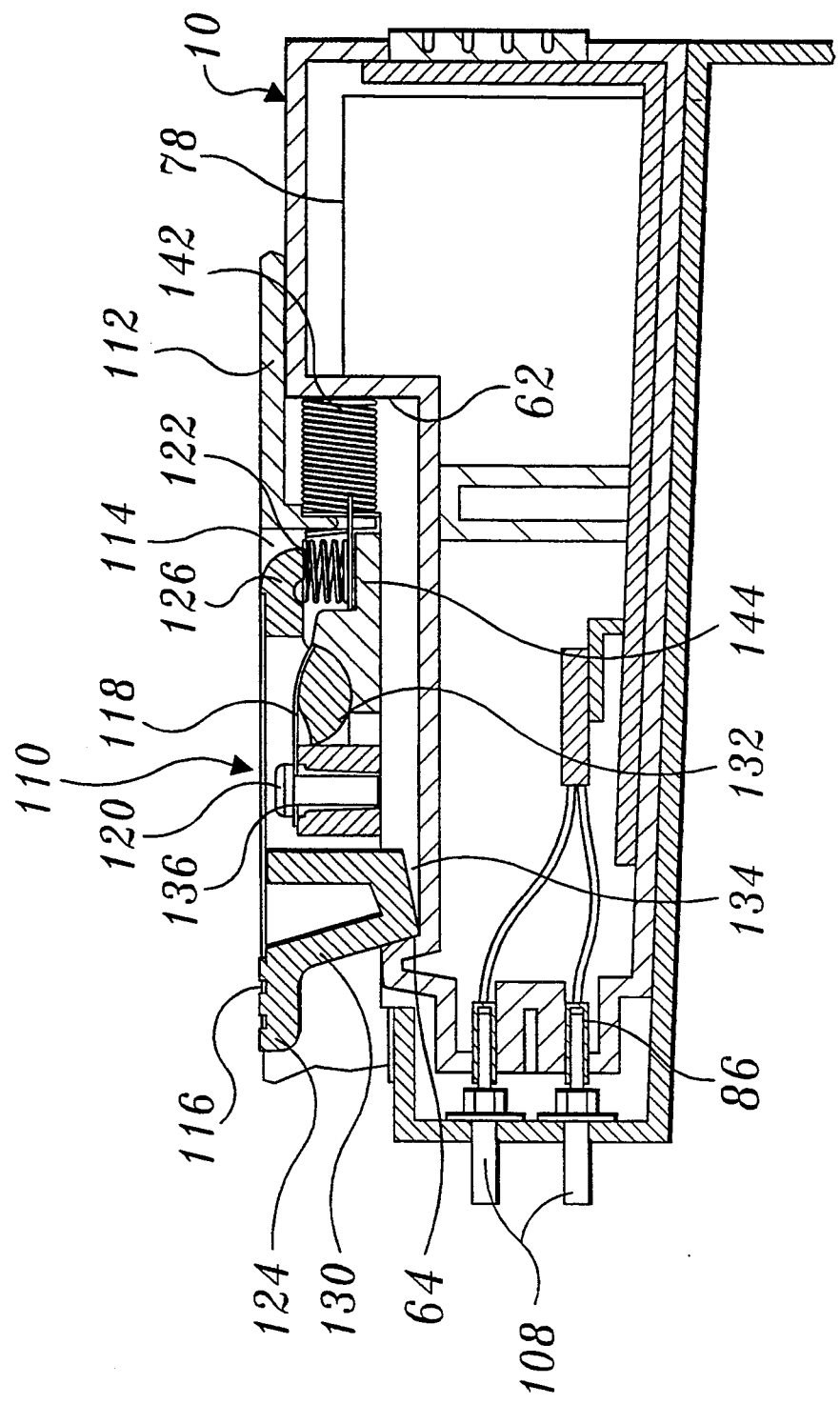

Continued insertion of the battery pack 10 eventually moves the latch surface 64 of the battery pack connector section 24 past the latch projection 130, as shown in FIGS. 6 and 7. At the point shown in FIG. 7, the bias spring 122 of latch assembly 110 pivots the latch arm 116, bringing the latch projection 130 securely into contact with the latch surface 64 on battery pack 10. As a result, movement of the battery pack 10 along the line of insertion is restricted.

At the point shown in FIG. 6, the free end of the ejection spring 142 comes in contact with the ejection surface 62, provided on the connector section 24 of the battery housing 14. The ejection spring 142 is received within a recess 154, defined by the top wall 50 of the connector section 24 of battery pack 10, at this point. Further insertion of the battery pack 10 into tray 98 compresses the ejection spring 142, as shown in FIG. 7. During this interval, the electrodes 108 provided on the defibrillator/monitor 12 will contact, and then fully engage, the receptacles 86 provided on the battery pack 10.

To remove the battery pack 10 from tray 98, the lift tab 124 of the latch arm 116 is manually lifted to the position shown in FIG. 6. As a result, the latch arm 116 pivots about the pivot bar 128, compressing the bias spring 122 and lifting the latch projection 130 from the projection opening 134. With the latch projection 130 disengaged from the latch surface 64 of the battery pack 10, the battery pack 10 can be withdrawn from tray 98 along the line of insertion. The force of the compressed ejection spring 142 against the ejection surface 62 of the battery pack 10 assists in the removal of battery pack 10.

As will be appreciated, the location of the latch assembly 110, ejection spring 142, and connectors 108 relative to the battery pack 10 is somewhat unusual. Rather than being aligned with a plane passing through the center of mass of the battery pack 10, which would allow the force of the ejection spring and latch assembly to act more directly on the mass of the battery pack, they are provided on one side of the battery pack 10. This side-by-side configuration is due, in part, to the constraints of instrument 12, yet allows a featurally complex but mechanically simple battery pack 10 to be developed. By ensuring the axial alignment of the ejection, connection, and latching mechanisms, the tendency of the side-mounted ejection spring 142 to provide a torque to the battery pack 10 during insertion and removal is reduced. As a result, the battery pack 10 can be easily, smoothly, and reliably connected to, and disconnected from, instrument 12.

Those skilled in the art will recognize that the embodiments of the invention disclosed herein are exemplary in nature and that various changes can be made therein without departing from the scope and the spirit of the invention. In this regard, and as was previously mentioned, the invention is readily embodied with various types of batteries and different circuits in the circuit board assembly. Further, it will be recognized that the relationship between the storage section and connector section of the battery pack may be varied, as desired. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A battery pack for use with a medical instrument including a latch, an ejector, and an electrical connector, said battery pack comprising:
   a housing including a battery storage section and a connector section, the connector section being disposed at a side of the battery storage section;
   energy storage means, disposed in the battery storage section, for storing electrical energy;
   connector engagement means, disposed on the connector section proximate to a front face of the housing;
   latch engagement means, disposed on the connector section, for engaging said latch;
   ejector engagement means, disposed on the connector section, for engaging said ejector; and
   wherein said latch engagement means, ejector engagement means, and connector engagement means are substantially aligned such that the latch engagement means is disposed between the connector engagement means and the ejector engagement means.

2. A battery pack, for use with a medical instrument having a handle and a battery tray constructed for receiving said battery pack, said instrument further including latch means, positioned adjacent one side of the battery tray, for releasably engaging said battery pack when introduced into the battery tray and ejection means, positioned adjacent the one side of the battery tray, for applying a resistive force to said battery pack when introduced into said battery tray, said battery pack comprising:
   a housing including a battery storage section and a connector section, said battery storage section including a front surface, back surface, first side, and second side, said connector section being positioned adjacent said first side of said battery storage section and including a recess formed, in part, by a latch surface and an ejection surface, said housing being receivable in the battery tray, said latch surface being for cooperatively engaging the latch means, said recess being for at least partially receiving the ejection means when said battery pack is introduced into the tray, and said ejection surface being for cooperatively engaging the ejection means when said battery pack is introduced into the battery tray;
   at least one battery, received within said battery storage compartment; and
   one or more connectors disposed on the connector section and aligned parallel to the front face of the housing for allowing said battery to be electrically connected to the instrument.

3. A method of connecting a battery pack to a medical instrument comprising the steps of:
   introducing the battery pack into a battery tray provided on the medical instrument;
   electrically coupling a connector provided at a side of the battery pack with a mating connector provided at a side of the battery tray;
   mechanically engaging a latch surface provided on the battery pack with a latch provided on the medical instrument; and
   contacting an ejection surface provided on the battery pack with an ejector provided on the instrument, said steps of electrically coupling, mechanically engaging, and contacting being performed in substantial alignment to allow the battery pack to be easily connected to the instrument.

4. A medical instrument, for use with a battery pack, said medical instrument comprising:
   a housing;
   handle means, coupled to said housing, for allowing said medical instrument to be carried by a user;
   battery storage means, provided in said housing of said instrument, for receiving the battery pack, said battery storage means being positioned so that the center of gravity of said medical instrument is substantially aligned with said handle of said instrument when a battery pack is received by said battery storage means;
   a latch arm, coupled to said housing adjacent said battery storage means, for releasably engaging a battery pack when the battery pack is received by the battery storage means, the latch arm having a latch projection that engages a corresponding latch surface disposed on the battery pack;
   an ejection spring, disposed in line with the latch arm and coupled to said housing adjacent said battery storage means, for applying a force to a battery pack such that the latch projection of the latch arm is forced against the latch projection of the battery pack when the battery pack is received by said battery storage means; and
   a plurality of electrical connectors coupled to said housing adjacent said battery storage means, the connectors being positioned about a common centerline and aligned with the ejection spring for electrically connecting the battery pack to said instrument.

* * * * *